United States Patent [19]

Chazot et al.

[11] Patent Number: 4,618,601

[45] Date of Patent: Oct. 21, 1986

[54] MEDICAMENTS BASED ON ZINC GLUCONATE USEFUL FOR THE TREATMENT OF HYPERPROLACTINAEMIAS

[75] Inventors: Guy Chazot, La Mulatiere; Catherine Suck, Sceaux, both of France

[73] Assignee: 501 Societe Civile de Recherches et d'Etudes Theraputiques, Antony, France

[21] Appl. No.: 804,099

[22] Filed: Dec. 3, 1985

[30] Foreign Application Priority Data

Dec. 7, 1984 [FR] France .................................. 84 18756

[51] Int. Cl.$^4$ ..................... A61K 31/70; A61K 31/315
[52] U.S. Cl. ...................................... 514/23; 514/494; 514/903
[58] Field of Search ........................... 514/23, 494, 903

[56] References Cited

U.S. PATENT DOCUMENTS

| 3,898,328 | 8/1975 | Beigler et al. | 514/23 |
| 3,928,574 | 12/1975 | Philips | 424/153 |
| 4,041,153 | 8/1977 | Howard | 514/494 |
| 4,064,234 | 12/1977 | Howard | 514/494 |
| 4,164,568 | 8/1979 | Bywater | 514/23 |
| 4,255,419 | 3/1981 | Leopold | 424/145 |

Primary Examiner—Douglas W. Robinson

[57] ABSTRACT

This invention relates to the use of zinc gluconate for making a medicament administered by the oral route and containing from 50 to 150 mg of zinc gluconate, said medicament being used for the treatment of hyperprolactinaemias.

2 Claims, No Drawings

MEDICAMENTS BASED ON ZINC GLUCONATE USEFUL FOR THE TREATMENT OF HYPERPROLACTINAEMIAS

The present invention relates to a novel medicament incorporating a strong dose of zinc gluconate, useful for the treatment of hyperprolactinaemias.

The use of salts of zinc, particularly the acetate, chloride, sulfate or gluconate, has already been recommended for the treatment of certain diseases. Ampoules exist on the market which each contain about 0.5 mg of salt of zinc, possibly associated with salts of copper or possibly with salts of nickel and cobalt.

A remarkably documented article has recently been published (Revue de Médecine, No. 32, October 1982), which relates to zinc, its physiological regulation in the human being and the disorders associated with deficiency or excess thereof. This publication suggests the possibility of daily administering zinc salts to patients at a dose of 10 to 45 mg of zinc per day for the treatment of states of nutritional deficiency in zinc and in particular for the treatment of acrodermatitis. However, in practice, it would seem that medicaments allowing large quantities of zinc to be administered are not to be found on the market at present.

It has now been found, and this is the subject matter of the present invention, that the novel medicaments, administered by the oral route, and containing, per unitary dose, from 50 to 150 mg of zinc gluconate, are useful for the treatment of hyperprolactinaemias, such as hyperprolactinaemias by hypophyseal adenoma, functional hyperprolactinaemias and iastrogenic hyperprolactinaemias. In the medicaments according to the invention, the zinc gluconate is advantageously in association with a pharmaceutically acceptable vehicle.

These medicaments may be in the form of solutions, tablets or capsules, the latter being the preferred form of presentation. It will be indicated by way of example that an average dosage of 200 mg of zinc gluconate, per os, in two doses, is suitable for the treatment of hyperprolactinaemias.

The invention is founded on the following two observations:

the remarkable gastric tolerance—more generally from the digestive standpoint—of the zinc gluconate, even when it is administered at high doses;

the fact that the hyperprolactinaemias mentioned above can be sensitive to a treatment based on zinc.

The non-toxicity of zinc gluconate at the doses used has, of course, been verified in the rat and in the human being.

The treatment of hyperprolactinaemias by zinc gluconate at high doses must be considered essentially as a preventive and/or maintenance treatment, i.e. a treatment followed regularly for several months.

The following examples illustrate the use of zinc gluconate at a high dose.

EXAMPLE 1C

Mrs. L. AIME

Mrs. L. AIME presented a hyperprolactinaemia in the course of an "empty sella syndrome". X-rays of the sella turcica showed an enlargement of the sella. A scanner examination showed an aspect of empty sella.

(1) The dosage of the basal prolactine without treatment was 30 $\mu g/l$ and rose to 59 $\mu g/l$ under the TRH ($\alpha$) test. The patient was then subjected to a treatment with the medicament according to the invention under the following conditions: administration for 15 days of 2 capsules containing 15 mg of zinc per day (at 10 a.m. and at 4 p.m.) without any other treatment. This treatment is hereinafter called "L 35 treatment".

(2) The dosage of the prolactine after L 35 treatment was 18 $\mu g/l$ and rose to 40 $\mu g/l$ under the TRH test. The TRH is the hypothalamic factor for release of thyrotrophine.

(3) A study of the gonadotropic function gave the following results: disappearance of the pulsatility of the LH (luteinizing hormone) under LHRH (hypothalamic factor for release of the luteinizing hormone) and reduction of the response.

EXAMPLE 2C

Mrs. L. YVETTE

Mrs. L. Yvette presented a hyperprolactinaemia in the course of a neuroleptics syndrome. The X-rays of the sella turcica were normal.

(1) The dosage of the basal prolactine without treatment was 60 $\mu g/l$ and rose to 80 $\mu g/l$ under TRH.

(2) The dosage of the prolactine after L 35 treatment was 40 $\mu g/l$ and rose to 56 $\mu g/l$ under TRH.

EXAMPLE 3C

Mrs. P

Mrs. P, 45 years old, presented a hyperprolactinaemia by microadenoma of the pituitary gland known for four years. The X-rays of the sella turcica showed a double bottom aspect.

(1) The dosage of the basal prolactine without treatment was 70 $\mu g/l$ and rose to 93 $\mu g/l$ in the course of the TRH test.

(2) Dosage of the prolactine after L 35 treatment: prolactine at 58 $\mu g/l$ rising to 64 $\mu g/l$ in the course of the TRH test.

(3) Study of the gonadotropic function: reduction of the pulsatility of LH under LHRH.

(4) TSH function: no modification.

What is claimed is:

1. A method of treating hyperprolactinaemias which comprises orally administering to a patient in need thereof from 50 to 150 mg of zinc gluconate.

2. The method of claim 1 wherein the medicament is in capsule form.

* * * * *